(12) United States Patent
Eidenschink

(10) Patent No.: US 8,784,472 B2
(45) Date of Patent: Jul. 22, 2014

(54) CLUTCH DRIVEN STENT DELIVERY SYSTEM

(75) Inventor: Tracee Eidenschink, Wayzata, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2939 days.

(21) Appl. No.: 10/641,488

(22) Filed: Aug. 15, 2003

(65) Prior Publication Data

US 2005/0038494 A1 Feb. 17, 2005

(51) Int. Cl.
*A61F 2/06* (2013.01)

(52) U.S. Cl.
USPC .......................................... 623/1.12; 606/108

(58) Field of Classification Search
USPC ............... 623/1.12, 1.35, 1.11; 606/194, 108, 606/198, 195; 604/96.01, 103.03, 103.05, 604/264
See application file for complete search history.

(56) References Cited

U.S. PATENT DOCUMENTS

| | | | |
|---|---|---|---|
| 4,448,195 A | 5/1984 | LeVeen et al. | 128/344 |
| 4,484,585 A | 11/1984 | Baier | 128/748 |
| 4,601,701 A | 7/1986 | Mueller, Jr. | 604/83 |
| 4,769,005 A | 9/1988 | Ginsburg et al. | 604/53 |
| 4,776,337 A | 10/1988 | Palmaz | 128/343 |
| 4,913,141 A | 4/1990 | Hillstead | 606/108 |
| 4,994,071 A | 2/1991 | MacGregor | 606/194 |
| 4,998,923 A | 3/1991 | Samson et al. | 606/194 |
| 5,019,085 A | 5/1991 | Hillstead | 606/108 |
| 5,122,154 A | 6/1992 | Rhodes | 606/198 |
| 5,147,387 A * | 9/1992 | Jansen et al. | 606/108 |
| 5,195,984 A | 3/1993 | Schatz | 606/195 |
| 5,219,355 A | 6/1993 | Parodi et al. | 606/191 |
| 5,316,023 A | 5/1994 | Palmaz et al. | 128/898 |
| 5,397,305 A | 3/1995 | Kawula et al. | 604/96 |
| 5,449,353 A | 9/1995 | Watanabe et al. | 604/96 |
| 5,477,856 A | 12/1995 | Lundquist | 128/642 |

(Continued)

FOREIGN PATENT DOCUMENTS

| | | |
|---|---|---|
| DE | 297 01 758 | 5/1997 |
| FR | 2 678 508 A1 | 1/1993 |

(Continued)

OTHER PUBLICATIONS

Foley et al., "Bifurcation Lesion Stenting", *The Thoraxcentre Journal*, vol. 8, No. 4, (1996).

(Continued)

*Primary Examiner* — Dianne Dornbusch
*Assistant Examiner* — Robert Lynch
(74) *Attorney, Agent, or Firm* — Seager, Tufte & Wickhem LLC

(57) ABSTRACT

A catheter assembly has an engaged state and an unengaged state comprising a proximal member having a longitudinal axis and a distal member having a longitudinal axis. A distal end of the proximal member is removably engageable to the distal member. The distal member has a first distal portion and a second distal portion, and the first distal portion is retractable from the second distal portion. In the engaged state the distal member is substantially freely rotatable about its longitudinal axis and in relation to the proximal member. In the engaged state the proximal member is constructed and arranged to be moved in a direction along the longitudinal axis such that proximal movement of the proximal member retracts at least the first distal portion of the distal member from at least the second distal portion.

20 Claims, 23 Drawing Sheets

(56) References Cited

U.S. PATENT DOCUMENTS

| | | | |
|---|---|---|---|
| 5,632,763 A | 5/1997 | Glastra | 606/194 |
| 5,643,278 A | 7/1997 | Wijay | 606/108 |
| 5,683,345 A | 11/1997 | Waksman et al. | 600/3 |
| 5,683,451 A * | 11/1997 | Lenker et al. | 623/1.11 |
| 5,697,971 A | 12/1997 | Fischell et al. | 623/1 |
| 5,725,519 A | 3/1998 | Penner et al. | 606/1 |
| 5,749,825 A | 5/1998 | Fischell et al. | 600/3 |
| 5,755,734 A | 5/1998 | Richter et al. | 606/194 |
| 5,755,735 A | 5/1998 | Richter et al. | 606/194 |
| 5,755,778 A | 5/1998 | Kleshinski | 623/1 |
| 5,772,669 A | 6/1998 | Vrba | 606/108 |
| 5,797,952 A * | 8/1998 | Klein | 623/1.12 |
| 5,873,906 A | 2/1999 | Lau et al. | 623/1 |
| 5,876,374 A | 3/1999 | Alba et al. | 604/96 |
| 5,893,868 A | 4/1999 | Hanson et al. | 623/1.11 |
| 5,906,640 A | 5/1999 | Penn et al. | 623/1 |
| 5,908,405 A | 6/1999 | Imran et al. | 604/53 |
| 5,921,995 A | 7/1999 | Kleshinski | 606/153 |
| 5,935,161 A | 8/1999 | Robinson et al. | 623/1 |
| 5,941,908 A | 8/1999 | Goldsteen et al. | 623/1 |
| 5,951,569 A | 9/1999 | Tuckey et al. | 606/108 |
| 5,957,929 A | 9/1999 | Brenneman | 606/108 |
| 5,961,546 A | 10/1999 | Robinson et al. | 623/1 |
| 5,961,548 A | 10/1999 | Shmulewitz | 623/1 |
| 6,013,092 A | 1/2000 | Dehdashtian et al. | 606/194 |
| 6,017,362 A | 1/2000 | Lau | 623/1 |
| 6,027,460 A | 2/2000 | Shturman | 600/585 |
| 6,033,434 A | 3/2000 | Borghi | 623/1 |
| 6,048,361 A | 4/2000 | Von Oepen | 623/1 |
| 6,056,722 A | 5/2000 | Jayaraman | 604/102 |
| 6,056,775 A | 5/2000 | Borghi et al. | 623/1.16 |
| 6,059,813 A * | 5/2000 | Vrba et al. | 606/198 |
| 6,071,286 A | 6/2000 | Mawad | 606/108 |
| 6,077,297 A | 6/2000 | Robinson et al. | 623/1.11 |
| 6,090,127 A | 7/2000 | Globerman | 606/194 |
| 6,096,073 A | 8/2000 | Webster et al. | 623/1.16 |
| 6,110,191 A | 8/2000 | Dehdashtian et al. | 606/192 |
| 6,117,156 A | 9/2000 | Richter et al. | 606/194 |
| 6,120,522 A | 9/2000 | Vrba et al. | 606/190 |
| 6,126,685 A * | 10/2000 | Lenker et al. | 623/1.11 |
| 6,132,450 A | 10/2000 | Hanson et al. | 606/198 |
| 6,143,014 A | 11/2000 | Dehdashtian et al. | 606/192 |
| 6,146,415 A | 11/2000 | Fitz | 623/1.11 |
| 6,152,944 A | 11/2000 | Holman et al. | 623/1.11 |
| 6,165,195 A | 12/2000 | Wilson et al. | 606/194 |
| 6,165,210 A | 12/2000 | Lau et al. | 623/1.12 |
| 6,187,015 B1 | 2/2001 | Brenneman | 606/108 |
| 6,190,360 B1 | 2/2001 | Iancea et al. | 604/164.09 |
| 6,190,393 B1 | 2/2001 | Bevier et al. | 606/108 |
| 6,210,380 B1 | 4/2001 | Mauch | 604/284 |
| 6,210,431 B1 | 4/2001 | Power | 623/1.11 |
| 6,221,090 B1 | 4/2001 | Wilson | 606/194 |
| 6,221,097 B1 | 4/2001 | Wang et al. | 623/1.11 |
| 6,224,587 B1 | 5/2001 | Gibson | 604/528 |
| 6,238,410 B1 * | 5/2001 | Vrba et al. | 606/198 |
| 6,246,914 B1 | 6/2001 | De la Rama et al. | 607/122 |
| 6,254,593 B1 | 7/2001 | Wilson | 606/1.11 |
| 6,258,052 B1 | 7/2001 | Milo | 604/22 |
| 6,258,073 B1 | 7/2001 | Mauch | 604/284 |
| 6,264,688 B1 | 7/2001 | Herklotz et al. | 623/1.16 |
| 6,287,277 B1 | 9/2001 | Yan | 604/96.01 |
| 6,287,330 B1 | 9/2001 | Johansson et al. | 623/1.13 |
| 6,290,673 B1 | 9/2001 | Shanley | 604/102.02 |
| 6,299,636 B1 | 10/2001 | Schmitt et al. | 623/1.2 |
| 6,319,275 B1 | 11/2001 | Lashinski et al. | 623/1.11 |
| 6,322,548 B1 | 11/2001 | Payne et al. | 604/500 |
| 6,361,544 B1 | 3/2002 | Wilson et al. | 606/194 |
| 6,361,555 B1 | 3/2002 | Wilson | 623/1.11 |
| 6,364,893 B1 | 4/2002 | Sahatjian et al. | 606/194 |
| 6,371,978 B1 | 4/2002 | Wilson | 623/1.11 |
| 6,375,660 B1 | 4/2002 | Fischell et al. | 606/108 |
| 6,379,372 B1 | 4/2002 | Dehdashtian et al. | 606/192 |
| 6,387,120 B2 | 5/2002 | Wilson et al. | 623/1.11 |
| 6,391,050 B1 | 5/2002 | Broome | 623/1.11 |
| 6,406,487 B2 | 6/2002 | Brenneman | 623/1.11 |
| 6,406,489 B1 | 6/2002 | Richter et al. | 623/1.16 |
| 6,416,529 B1 | 7/2002 | Holman et al. | 606/194 |
| 6,436,104 B2 | 8/2002 | Hojeibane | 606/108 |
| 6,443,980 B1 | 9/2002 | Wang et al. | 623/1.35 |
| 6,475,166 B1 | 11/2002 | Escano | 600/585 |
| 6,482,211 B1 | 11/2002 | Choi | 606/108 |
| 6,482,227 B1 * | 11/2002 | Solovay | 623/1.13 |
| 6,488,694 B1 | 12/2002 | Lau et al. | 606/194 |
| 6,508,835 B1 | 1/2003 | Shaolian et al. | 623/1.35 |
| 6,514,281 B1 | 2/2003 | Blaeser et al. | 623/1.12 |
| 6,520,983 B1 | 2/2003 | Colgan et al. | 623/1.11 |
| 6,520,988 B1 | 2/2003 | Colombo et al. | 623/1.35 |
| 6,527,789 B1 * | 3/2003 | Lau et al. | 606/194 |
| 6,530,947 B1 | 3/2003 | Euteneuer et al. | 623/1.11 |
| 6,533,805 B1 | 3/2003 | Jervis | 623/1.11 |
| 6,540,719 B2 | 4/2003 | Bigus et al. | 604/96.01 |
| 6,554,841 B1 | 4/2003 | Yang | 606/108 |
| 6,572,643 B1 | 6/2003 | Gharibadeh | 623/1.11 |
| 6,582,459 B1 | 6/2003 | Lau et al. | 623/1.11 |
| 6,589,262 B1 | 7/2003 | Honebrink et al. | 606/191 |
| 6,599,315 B2 | 7/2003 | Wilson | 623/1.11 |
| 6,602,226 B1 | 8/2003 | Smith et al. | 604/103.05 |
| 6,607,506 B2 | 8/2003 | Kletschka | 604/96.01 |
| 6,613,067 B1 | 9/2003 | Johnson | 606/194 |
| 6,629,981 B2 | 10/2003 | Bui et al. | 606/108 |
| 6,827,731 B2 * | 12/2004 | Armstrong et al. | 623/1.12 |
| 6,908,477 B2 * | 6/2005 | McGuckin et al. | 623/1.11 |
| 2001/0001128 A1 | 5/2001 | Holman et al. | 623/1.11 |
| 2001/0049548 A1 | 12/2001 | Vardi et al. | 623/1.11 |
| 2002/0019664 A1 | 2/2002 | Douglas | 623/1.35 |
| 2002/0019665 A1 | 2/2002 | Dehdashtian et al. | 623/1.35 |
| 2002/0022874 A1 | 2/2002 | Wilson | 623/1.11 |
| 2002/0038140 A1 | 3/2002 | Yang et al. | 623/1.12 |
| 2002/0038141 A1 | 3/2002 | Yang et al. | 623/1.12 |
| 2002/0072755 A1 * | 6/2002 | Bigus et al. | 606/108 |
| 2002/0111675 A1 | 8/2002 | Wilson | 623/1.35 |
| 2002/0116045 A1 | 8/2002 | Eidenschink | 623/1.11 |
| 2002/0120320 A1 | 8/2002 | Wang et al. | 623/1.11 |
| 2003/0055484 A1 | 3/2003 | Lau et al. | 623/1.13 |
| 2003/0191516 A1 | 10/2003 | Weldon et al. | 623/1.12 |
| 2003/0195546 A1 | 10/2003 | Solar et al. | 606/192 |
| 2003/0199966 A1 * | 10/2003 | Shiu et al. | 623/1.12 |
| 2004/0087977 A1 * | 5/2004 | Nolan et al. | 606/142 |

FOREIGN PATENT DOCUMENTS

| | | |
|---|---|---|
| WO | 96/37167 | 11/1996 |
| WO | 98/53761 | 12/1998 |
| WO | 03/017872 A1 | 3/2003 |
| WO | 03/055414 | 7/2003 |

OTHER PUBLICATIONS

Schampaert, MD, Erick et al., "The V-Stent: A Novel Technique for Coronary Bifurcation Stenting", *Catheterization and Cardiovascular Diagnosis*, 39:320-326 (1996).

Pomerantz, MD, et al., "Distortion of Palmaz-Schatz Stent Geometry Following Side-Branch Balloon Dilation Through the Stent in a Rabbit Model", *Catheterization and Cardiovascular Diagnosis*, 40:422-426 (1997).

Palmaz, MD, et al., "Aortic Bifurcation Stenosis: Treatment with Intravascular Stents", *Journal of Vascular and Interventional Radiology*, vol. 2, No. 3, pp. 319-323 (Aug. 1991).

Oda, MD., et al., "Fork Stenting for Bifurcational Lesion", Journal of Interventional Cardiology, vol. 9, No. 6, pp. 445-454 (Dec. 1996).

Nakamura et al., "Techniques for Palmaz-Schatz Stent Deployment in Lesions With a Large Side Branch", Catheterization and Cardiovascular Diagnosis, vol. 34, pp. 353-361 (1995).

U.S. Appl. No. 10/375,689, filed Feb. 27, 2003, Eidenschink.
U.S. Appl. No. 10/747,546, filed Dec. 29, 2003, Eidenschink et al.

* cited by examiner

CLUTCH DRIVEN STENT DELIVERY SYSTEM

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

At least one embodiment of the present invention is directed to the field stent delivery systems used to treat stenoses, and more particularly to stenoses at a bifurcation of a passage.

2. Description of the Related Art

Stent systems are widely used in the treatment of stenoses. Intravascular stents are used in coronary, renal, and carotid arteries, for example, to maintain an open passage through the artery. In patients whose coronary heart disease consists of focal lesions, stents have proven effective. For example, where only a single coronary artery is clogged or where there are short blockages in more than a single artery, stents have been used with a great amount of success. An intravascular stent may be positioned in a clogged artery by a catheter assembly and is often set in place by inflating a balloon upon which the stent is mounted. This expands the diameter of the stent and opens the previously clogged artery. The balloon is then deflated and removed from the patient while the stent retains an open passage through the artery.

It is recognized, however, that a stent can be deployed in manners other than inflating and deflating a balloon. For example, self-expanding stents have been developed in which a cover is removed from over a stent, thereby allowing the stent to deploy or spring into place. It is also contemplated that other deployment mechanisms or means may be used or developed to advantageously deliver and deploy a stent in position.

Nevertheless, a need still exists for properly delivering and locating a stent at a bifurcation. Although efforts have been made to use a stent at bifurcations, these sites have previously been inadequately treated by a stent. For example, U.S. Pat. No. 5,749,825, the entire contents of which being incorporated herein by reference, is representative of a catheter assembly system that treats stenoses at an arterial bifurcation.

A stent having different diameters has been proposed to allow placement in both a main passage, such as an artery, and a side branch passage, such as a continuation branch artery. Additionally, these stents generally have an opening which allows for unimpeded blood flow into the side branch artery. However, problems are still encountered in orienting the stent relative to the side branch at the bifurcation of the main and branch passages.

Many current devices rely on either passive torque (e.g., pushing the stent forward and allowing the stent that is fixed on the guide wire/balloon to passively rotate itself into place) or creating torque from outside of the patient to properly orient the stent delivery system in the passage. These devices and methods of achieving proper angular orientation have not been shown to be effective in properly placing and positioning the stent. As will be appreciated and understood by those skilled in the art, improper placement of the stent with respect to its rotational or circumferential orientation, or its longitudinal placement, could lead to obstruction of the side branch passage. It is important to properly position or center an opening formed in the bifurcated stent with the side branch passage to maximize flow therethrough.

Thus, a need exists for effectively treating stenosed passage bifurcations. This need includes more precise and exact longitudinal placement and rotational/circumferential orientation of the stent.

Commercially available devices do not maintain side branch access at the time of stent deployment. This results in the potential for plaque shift and occlusion of the side branch passage.

It would also be advantageous if stents could be placed across the side branch while wire position is maintained thereby helping to protect and secure further access to the side branch.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment the catheter assembly has a longitudinal axis and has an engaged state and an unengaged state. In at least one embodiment the catheter assembly comprises a proximal member and a distal member. In at least one embodiment the distal member has a first distal portion and a second distal portion and the first distal portion may be constructed and arranged to be retractable from the second distal portion. In at least one embodiment the distal member and the proximal member are substantially moveable independent of one another in the unengaged state. In at least one embodiment while in the engaged state, a distal end of the proximal member may be engaged to at least a portion of the distal member and the distal member may be substantially freely rotatable about the longitudinal axis and in relation to the proximal member. In at least one embodiment while in the engaged state, the proximal member may be constructed and arranged to be moved in a direction along the longitudinal axis such that proximal movement of the proximal member in the engaged state retracts at least the first distal portion of the distal member from at least the second distal portion.

In at least one embodiment the distal member comprises a retractable sheath. In at least one embodiment the first distal portion comprises the sheath.

In at least one embodiment the sheath defines a slit, and the sheath has edges along the length of the slit.

In at least one embodiment the slit extends distally from a position on the sheath distal to the proximal most portion of the sheath.

In at least one embodiment the slit may be substantially parallel to the longitudinal axis.

In at least one embodiment the slit may be in the form of a wave. In at least one embodiment the slit may be in the form of a spiral.

In at least one embodiment the slit has an open configuration and a closed configuration. In at least one embodiment in the closed configuration, the edges of the sheath are retained together with a holding member. In at least one embodiment in the open configuration the holding member may be removed from the edges to open the slit.

In at least one embodiment the slit in the open configuration allows for retraction of the sheath along a first guidewire in a primary body lumen without removing a second guidewire in a secondary body lumen at the bifurcation site.

In some embodiments the holding member may be a wire or thread used in lacing up the slip. In some embodiments the holding member may be not removed, rather one portion of the holding member on one side of the slit may be separated from another portion of the holding member on another side of the slit. In some embodiments the member may be compatible with hook and loop material wherein the sheath and/or the holding member may include hook and loop material. Snaps, buttons, screws, adhesives, and/or magnetic material may be used as the holding member in at least some embodiment. In at least one embodiment the sheath comprises a distal sheath and a proximal sheath. In at least one embodiment in the engaged state the distal sheath may be retracted proximally and the proximal sheath may be retracted distally when the proximal member may be moved in the proximal direction.

In at least one embodiment the stent has an unexpanded configuration and an expanded configuration. In at least one embodiment in the unexpanded configuration the stent may be disposed about at least a portion of the second distal portion of the distal member.

In at least one embodiment the stent may be expanded from the unexpanded configuration to the expanded configuration when the first distal portion of the distal member may be retracted from the second distal portion of the distal member.

In at least one embodiment the stent may be selected from at least one member of the group consisting of self-expanding stents, inflation expandable stent, hybrid expandable stents and any combination thereof.

In at least one embodiment the stent may be a bifurcated stent.

In at least one embodiment the bifurcated stent has a pant configuration.

In at least one embodiment at least a portion of the first distal portion of the distal member defines a clutch housing and at least a portion of the proximal member defines a clutch extension. In at least one embodiment in the engaged state the clutch extension may be engaged to the clutch housing.

In at least one embodiment the clutch extension comprises a balloon portion having an unexpanded state and an expanded state. In at least one embodiment in the unengaged state the balloon may be in the unexpanded state such that the balloon portion may pass through the clutch housing. In at least one embodiment in the engaged state the balloon may be expandable to the expanded state such that the balloon portion may be retainingly engaged by the clutch housing.

In at least one embodiment the clutch extension comprises an expansion portion with fingers having an unexpanded state and an expanded state. In at least one embodiment in the unengaged state the fingers are in the unexpanded state such that the expansion portion may be constructed and arranged to allow the fingers to pass through the clutch housing. In at least one embodiment in the engaged state the fingers are expandable to the expanded state such that the expansion portion may be retainingly engaged by the clutch housing.

In at least one embodiment the fingers are constructed of a self-expanding material.

In at least one embodiment the fingers are constructed of nitinol.

In at least one embodiment at least a portion of the first distal portion of the distal member comprises a first magnetic portion on its proximal portion and the proximal member comprises a second magnetic portion on its distal portion. In at least one embodiment in the engaged state the first magnetic portion may be magnetically engaged to the second magnetic portion.

In at least one embodiment the catheter assembly comprises a barrier member having a first position and a second position. In at least one embodiment the barrier member may be constructed and arranged to substantially interfere with magnetic attraction between the first magnetic portion and the second magnetic portion. In at least one embodiment in the first position the barrier member may be between the first magnetic portion and the second magnetic portion. In at least one embodiment, in the second position the barrier member may be removed. In at least one embodiment in the unengaged state the barrier member may be in the first position. In at least one embodiment in the engaged state the barrier member may be in the second position.

In at least one embodiment the first magnetic portion and the second magnetic portion are magnetically engaged by an electromagnetic current.

In at least one embodiment the clutch extension comprises a grappling base having distally extending extensions. In at least one embodiment the grappling base has a forward position and a back position. In at least one embodiment in the forward position the grappling base is constructed and arranged such that the extensions engage the clutch housing of the distal member, and in the back position the grappling base is constructed and arranged such that the extensions extend to a position proximal to the clutch housing of the distal member. In at least one embodiment in the engaged state the grappling base may be in the forward position, and in the unengaged state the grappling base may be in the back position.

In at least one embodiment the grappling base is rotatable within the proximal member.

In at least one embodiment the clutch housing comprises a connecting portion selected from the group consisting of a looped wire ring, a looped polymer ring, a locking wire ring, a locking polymer ring, and any combination thereof.

In at least one embodiment the clutch housing comprises a rotating portion constructed and arranged to rotate independently of the sheath.

In at least one embodiment at least a portion of the distal end of the proximal member defines a clutch housing and at least a portion of the first distal portion of the distal member defines a clutch extension. In at least one embodiment the clutch extension comprises proximally extending extensions which have a proximally extending position and a relaxed position. In at least one embodiment in the proximally extending position the extensions are constructed and arranged such that the extensions engage the clutch housing of the proximal member, and in the relaxed position the extensions do not engage the clutch housing. In at least one embodiment in the engaged state the extensions are in the proximally extending position, and in the unengaged state the extensions are in the relaxed position.

In at least one embodiment the extensions are constructed and arranged with materials selected from the group consisting of magnetically attracted materials, shape memory materials, and any combination thereof.

In at least one embodiment the extensions are constructed and arranged such that a pull back member can pull the extensions proximally back to engage the proximal member.

In at least one embodiment the proximal member comprises on its distal portion a clutch housing which is constructed and arranged to rotate substantially about the longitudinal axis.

In at least one embodiment the clutch extension rotates substantially about the longitudinal axis and substantially independent of other portions of the distal member.

In at least one embodiment the distal member comprises a balloon.

In at least one embodiment the balloon comprises the first distal portion and is substantially freely rotatable about the longitudinal axis.

In at least one embodiment the proximal member comprises inflatable protuberances positioned substantially at the distal end of the balloon and positioned substantially at the proximal end of the balloon. In at least one embodiment the protuberances have an inflated state and an uninflated state. In at least one embodiment in the inflated state the protuberance forms a seal with the balloon such that in the unengaged state all the protuberances are in the uninflated state and such that in the engaged state one or more inflatable protuberances are in the inflated state.

In at least one embodiment during and after rotation the inflated protuberances form a seal with the balloon.

In at least one embodiment the proximal member is a wire.

In at least one embodiment the catheter assembly is in the engaged state prior to entry into a lumen.

In at least one embodiment the method of preassembling the catheter may be done such that the proximal member is engaged to the distal member such that the assembly is in the engaged state before entry into the lumen.

In at least one embodiment the method of preassembling the catheter may be done such that the distal member and the proximal member are engaged such that the assembly is permanently in the engaged state.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
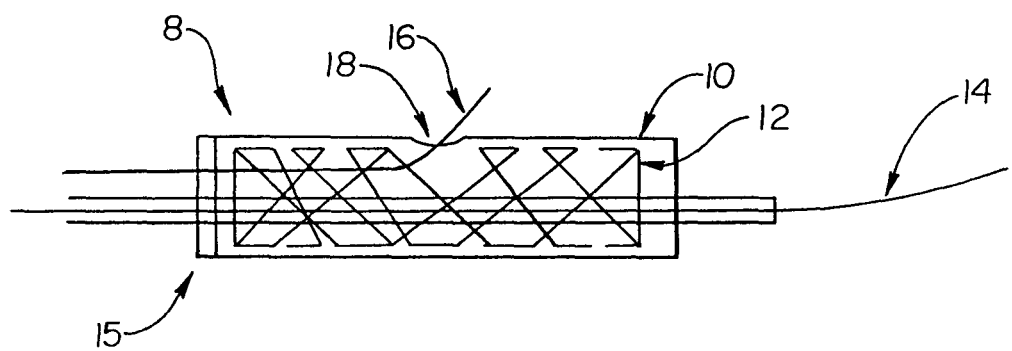
FIG. 1 is a side view of an embodiment of the invention wherein a catheter assembly having a slit sheath configuration is illustrated.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

In FIG. 1 a side view of an embodiment of a distal member 8 of the invention is shown. Here the sheath 10 covers a stent 12 having a first guidewire 14 and a second guidewire 16 passing through it. Such a stent 12 can be used in a vessel bifurcation. In some embodiments the distal member 8 is advanced along two guide wires 14 and 16. The first guidewire 14 is positioned in the primary passage or branch vessel and the second guidewire 16 diverges from the first guidewire 14 upon passage into the secondary branch in the region of the bifurcation. As the distal member 8 approaches the bifurcation, the sheath 10 may then rotate so as to be aligned with the side wall passage at the bifurcation.

Figure 2:
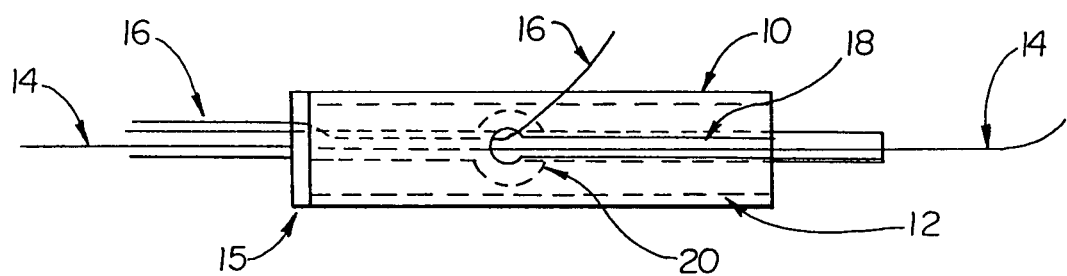
FIG. 2 is a partial top down view of the catheter assembly shown in FIG. 1 wherein an embodiment of the sheath is illustrated.

The sheath 10 has a slit 18 which allows the sheath 10 to be retracted without first removing second guidewire 16. The sheath 10 is engaged to stent sheath clutch housing 15. The different embodiments of the mechanism 15 are shown in detail in later figures. In at least one embodiment the sheath 10 is retracted before the stent 12 is deployed. In FIG. 2 a partial top down view of the catheter assembly 8 shown in FIG. 1 is illustrated. Here the stent 12 has a special cell 20 that provides structure through which another medical device may pass. In at least one embodiment, the special cell 20 may extend at an oblique angle into the bifurcation.

Figure 3:
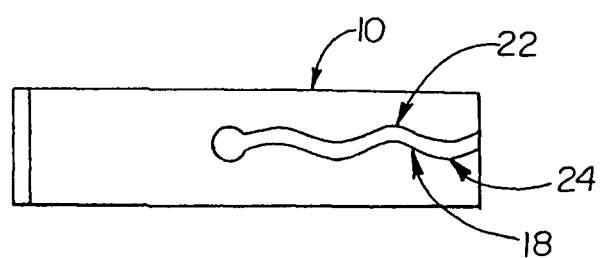
FIG. 3 is a partial top down view of the catheter assembly shown in FIG. 1 wherein an embodiment of the sheath is illustrated.

Due to the loads on the slit 18 in the sheath 10, in some embodiments it may be desirable to provide the slit with a variety of configurations. For example, in the embodiment shown in FIG. 3, the slit 18 has a substantially s-shaped configuration. Such a substantially s-shaped slit may prevent the stent 12 from trying to force itself into a non-round position beneath the sheath 10. The substantially s-shaped slit 18 may comprise a variety of different shapes, lengths, and configurations. For example, in the embodiment shown the slit 18 comprises two peaks 22 and valleys 24. The magnitude of the peaks and valleys may be substantially similar. However, in some embodiments a far greater number of peaks 22 and valleys 24 may be beneficial. Additionally, in some embodiments a far wider array of magnitudes for both the peaks and/or valleys may be beneficial.

Figure 4:
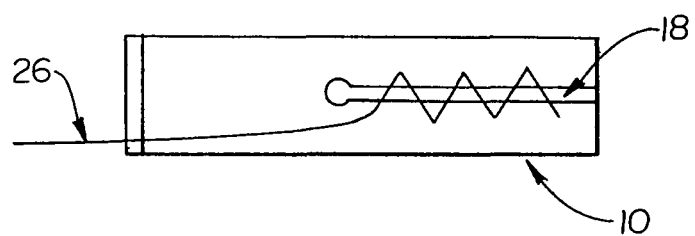
FIG. 4 is a partial top down view of the catheter assembly shown in FIG. 1 wherein an embodiment of the sheath is illustrated.

In some embodiments the slit 18 may be held together with a holding member 26. In some embodiments it may be beneficial to provide the slit 18 with a variety of holding members. In some such embodiments hook and loop material, snaps, buttons, screws, adhesives, and/or magnetic material, etc may be used as the holding member 26. For example, in the embodiment shown in FIG. 4, the holding member 26 is a thread which can lace the edges of the slit together and can be unraveled prior to the pulling of the sheath 10 or as the sheath 10 is being retracted.

Figure 5:
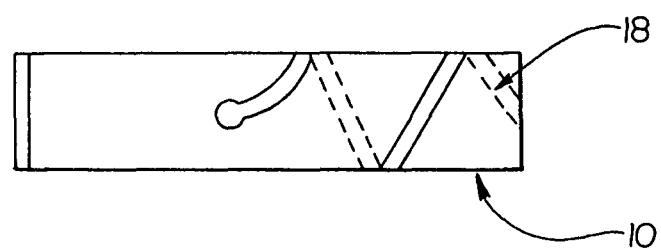
FIG. 5 is a partial top down view of the catheter assembly shown in FIG. 1 wherein an embodiment of the sheath is illustrated.

In other embodiments the slit 18 of the sheath 10 may have spiraled configurations. One such embodiment is shown in FIG. 5. In order to retract the sheath 10 it may be useful to employ a "smart" manifold and a small clutch to rotate the sheath 10 off at the same pitch of spiral as that of the spiral slit 18. It may be beneficial in some embodiments to combine the substantially s-shaped slit or the spiral slit of with the lacing of FIG. 4.

Figure 6:
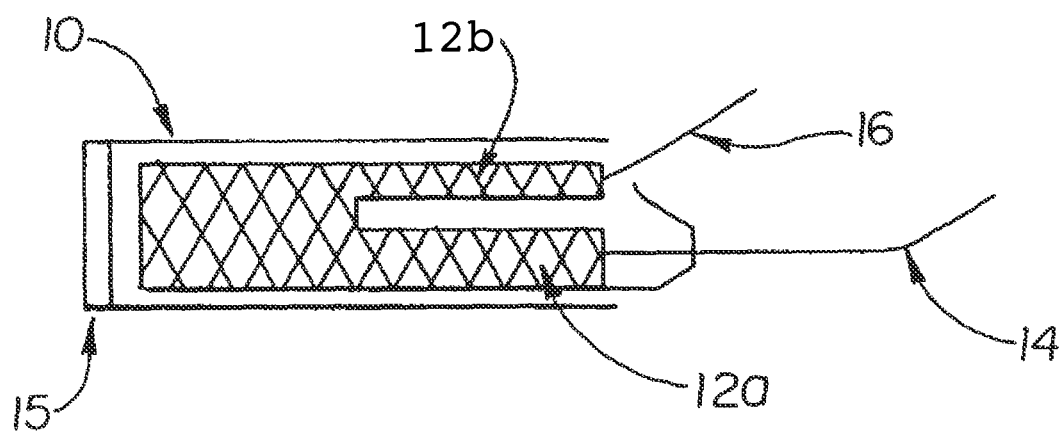
FIG. 6 is a side view of an embodiment of the invention wherein the catheter assembly is configured for delivery of a pant style bifurcated stent.

In some embodiments the slit 18 may be unnecessary. For example, in the embodiment shown in FIG. 6 the stent may be of the sort illustrated having a pant leg design. The stent 12 has two longitudinal portions wherein the first longitudinal portion 12a is disposed about first guidewire 14 along the length of first longitudinal portion 12a and second longitudinal portion 12b is disposed about second guidewire 16 along the length of second longitudinal portion 12b. In this embodiment the stent may have a self expanding pant design. Here, there is a single sheath 10 covering the stent 12 and longitudinal portions 12a and 12b. The second longitudinal portion 12b of the stent 12 is disposed about second guidewire 16 while the first longitudinal portion 12a of the stent 12 is disposed about first guidewire 14 passing through the tip of the stent end of the delivery system 28.

Figure 7:
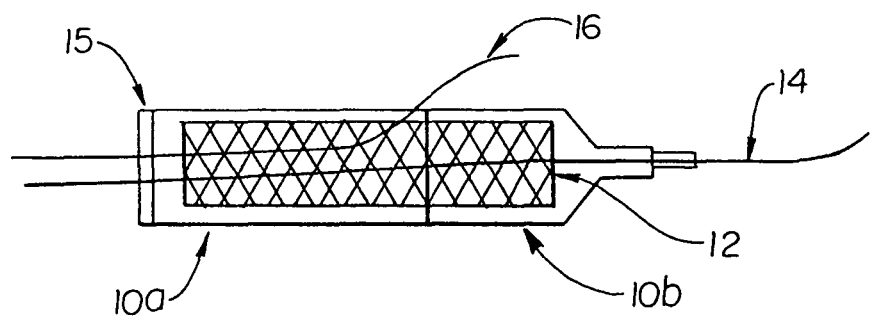
FIG. 7 is a side view of the embodiment of the invention wherein the catheter assembly comprises a proximal sheath and a distal sheath.

In some embodiments the sheath 10 is split into a proximal sheath portion 10a and a distal sheath portion 10b as illustrated in FIG. 7. The distal sheath portion 10b may be moved distally while the proximal sheath portion 10a may be moved proximally, thus allowing the stent 12 to expand from the center of the stent 12 to the ends of the stent 12 rather than from one end of the stent 12 to another (e.g. from the distal end to the proximal end).

Figure 8:
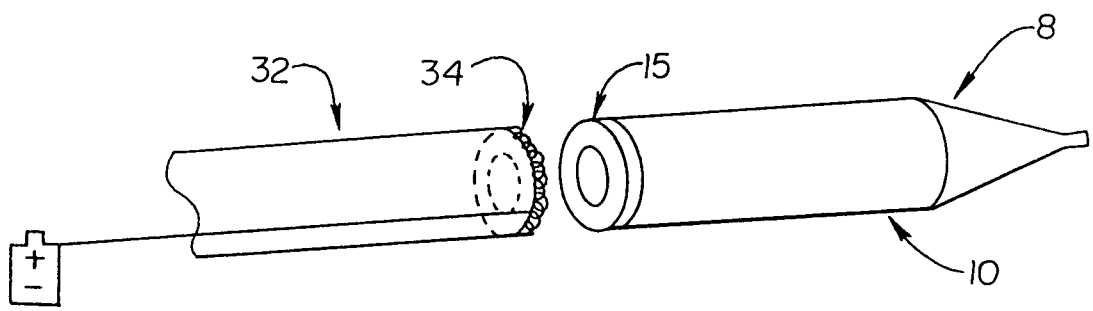
FIG. 8 is a perspective view of an embodiment of the invention wherein the proximal member and the distal member are separated.
Figure 9:
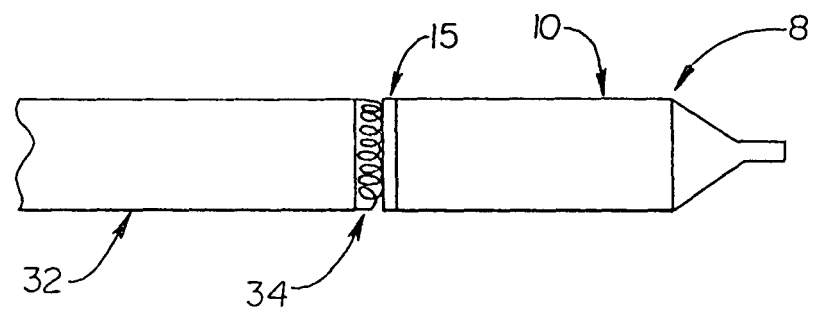
FIG. 9 is a side view of the embodiment shown in FIG. 8 in the engaged state.

In FIG. 8 an embodiment of the invention is shown wherein the sheath 10 is disposed over the distal member 8 of the catheter assembly. Though many geometrical shapes may be used, in at least one embodiment the stent sheath clutch housing 15 is oval shaped and has a magnetically attracted surface. The clutch housing 15 may be able to rotate about the catheter assembly. The distal end of the proximal member 32 comprises a magnetic configuration 34 which may be able to rotate. In this embodiment when an electric current is applied to the configuration 34 substantial magnetic properties may be produced and the distal end of the proximal member 32 engages stent sheath clutch housing 15 of the distal member 8 such that the stent sheath 10 may be retracted by retracting the proximal member 32. Proximal member 32 and the distal member 8 are shown engaged in FIG. 9. The magnetic attraction between stent sheath clutch housing 15 and magnetic configuration 34 substantially disappears when current is no longer flowing to the configuration 34.

In some embodiments, the configuration 34 may also be a permanent magnet. In at least one embodiment the proximal member 32 and stent sheath clutch housing 15 may be advanced with a barrier member 36 between them. When the barrier member 36 is removed the attractive forces between the clutch housing 15 and the configuration 34 on proximal member 32 may be capable of retracting stent sheath 10 upon moving the proximal member 32 in a proximal direction.

Figure 11:
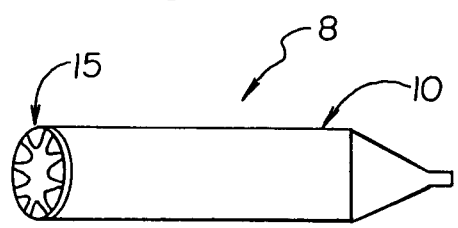
FIGS. 11 and 12 are side views of an embodiment of the invention wherein the sheath engagement mechanism and pull back mechanism are shown.
Figure 12:
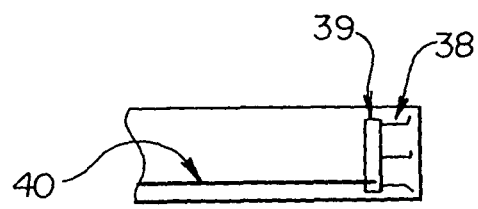
Figure 13:
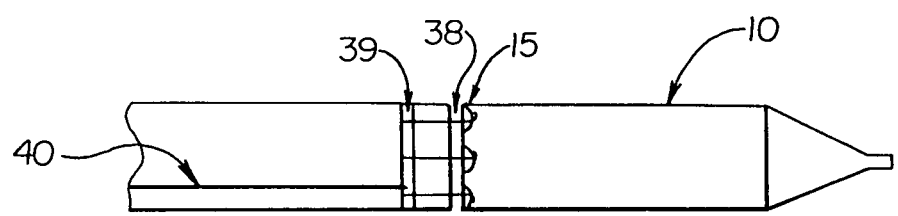
FIG. 13 is a side view of the embodiment of FIGS. 11 and 12 wherein the catheter assembly is shown in the engaged state.

In at least one embodiment the distal member 8 may have a clutch housing 15 of a looped wire (metallic or polymer) ring and/or a metallic or polymer locking ring which may consist of a band disposed inside or outside distal member 8. At least one embodiment is shown in FIG. 11 where a looped wire ring may be included. The hooks 38 of FIG. 12 may be attached to grappling base 39 which can be pushed forward by distal movement of push/pull wire 40. The hooks 38 may be extended distally beyond the distal most portion of proximal member 32 and engage the clutch housing 15 of distal member 8. Once engaged as illustrated in FIG. 13, proximal movement of the proximal member 32 or proximal movement of push/pull wire 40 may retract sheath 10.

Figure 10:
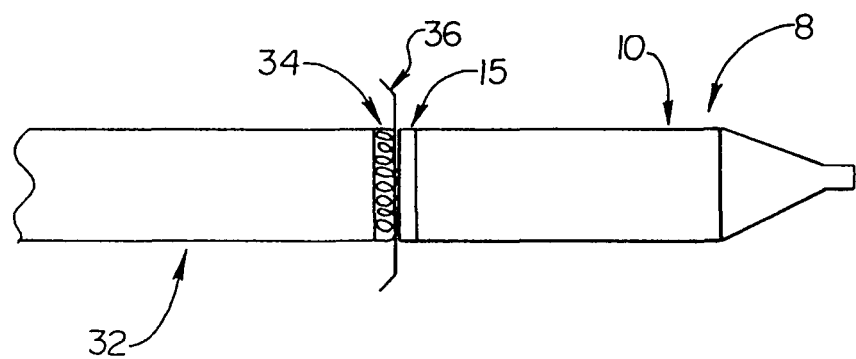
FIG. 10 is a side view of the embodiment shown in FIG. 8 in the unengaged state with a barrier member.
Figure 14:
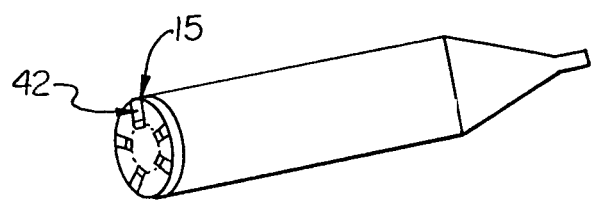
FIG. 14 is a perspective view of the distal member with clutch housing shown.
Figure 15:
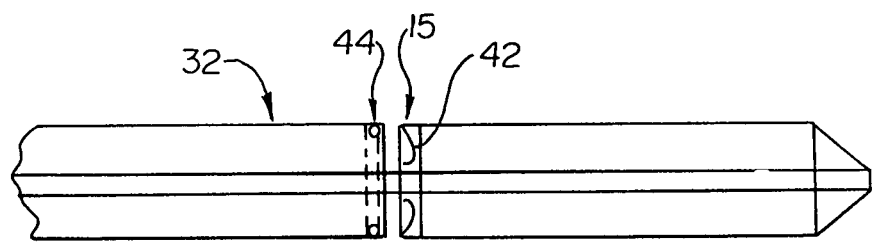
FIG. 15 is a side view of an embodiment shown in FIG. 14 unengaged to the proximal member.
Figure 16:
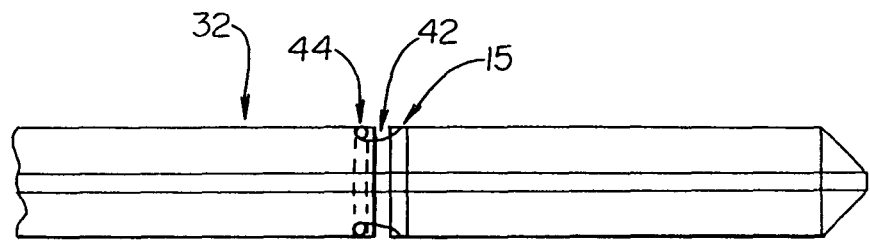
FIG. 16 is a side view of an embodiment shown in FIG. 14 engaged to the proximal member.

In at least one embodiment, as shown in FIG. 14, the clutch housing 15 may have hooks 42 which can be restrained from extending proximally with an intervening device or barrier member 36 as in FIG. 10. The clutch housing 15 having hooks 42 may be of a shape memory material that returns to an original extended shape upon heating. For example, when the hooks 42 are heated by the warmth of the body lumen or by electrical resistance they may extend proximally from clutch housing 15. The clutch housing 15 in at least one embodiment may have hooks 42 which are magnetically attracted to extend proximally towards the proximal member 32. This may comprise an electrically induced magnetic attraction. A pullwire may also be used to pull the hooks 42 proximally from the clutch housing 15. In all instances above, the hooks 42 are intended to engage the proximal member 32 through proximal member engagement mechanism 44 arranged about the opening of the proximal member 32. The mechanism 44 in some embodiments may be wire loop rings arranged about the distal opening of the proximal member 32 or a lock ring arranged about the distal opening of the proximal member 32 as shown in FIGS. 15 and 16.

Figure 17:
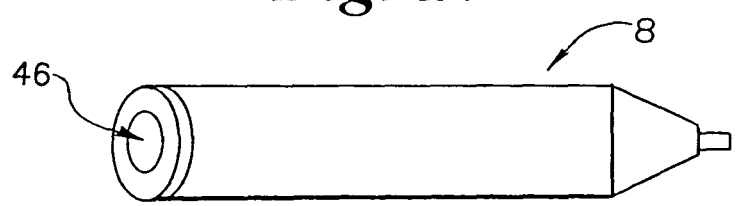
FIG. 17 is a perspective view of the distal member with clutch housing and through hole shown.
Figure 18:
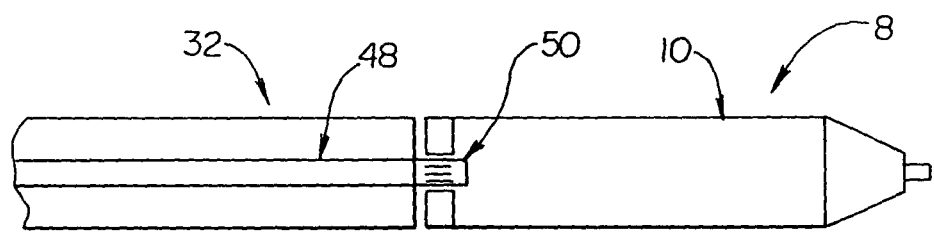
FIG. 18 is a side view of an embodiment shown in FIG. 17 unengaged to the proximal member.
Figure 19:
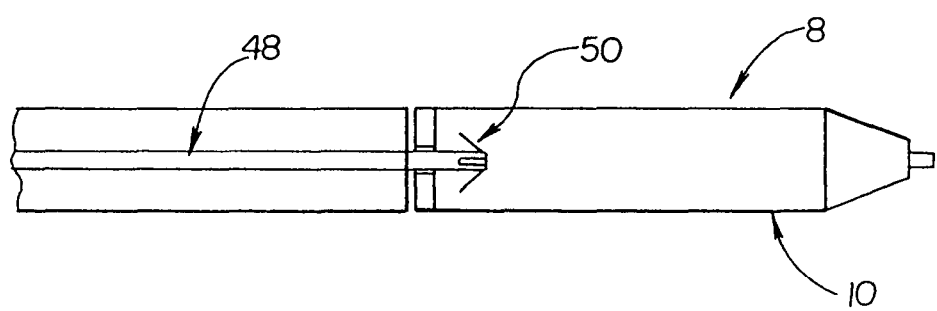
FIG. 19 is a side view of an embodiment shown in FIG. 17 engaged to the proximal member.

In at least one embodiment a distal member 8 has a through hole 46. For example, the distal member 8 of FIG. 17 illustrates at least one embodiment. Proximal member 32 may be positioned such that inner clutch extension 48 extends into through hole 46. For example, at least one embodiment is shown in FIG. 18. Inner clutch extension 48 may have expanding fingers 50 on its distal end. The distal member 8 may rotate around the expanding fingers 50 much like bearings. As shown in FIG. 19, upon the inner clutch extension 48 being advanced distally, the fingers 50 may expand such that proximal retraction of the inner clutch extension 48 may retract the sheath 10 as well.

Figure 20:
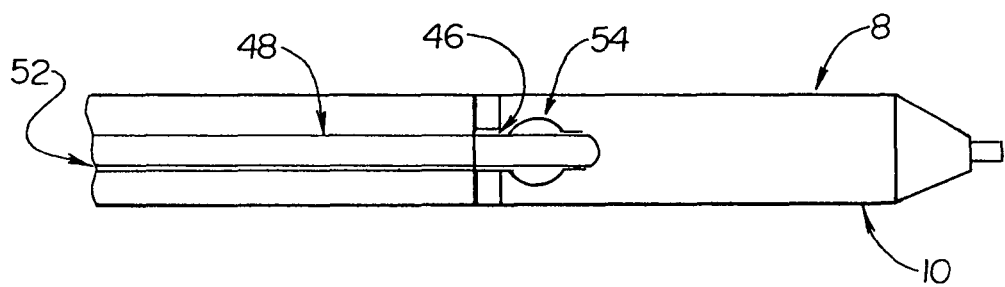
FIG. 20 is a side view of an embodiment of the invention in the engaged state.

As illustrated in FIG. 20, the clutch extension 48 may comprise an inflation lumen 52 for inflating balloon 54. Before insertion into the through hole 46 the balloon 54 may be partially inflated or the balloon may be deflated in order for the clutch extension 48 to pass through through hole 46. Upon insertion, the balloon 54 may be inflated thereby inhibiting the proximal motion of clutch extension 48 in relation to through hole 46. Thus, proximal motion of the clutch extension 48 may result in the sheath 10 being retracted.

Figure 21:
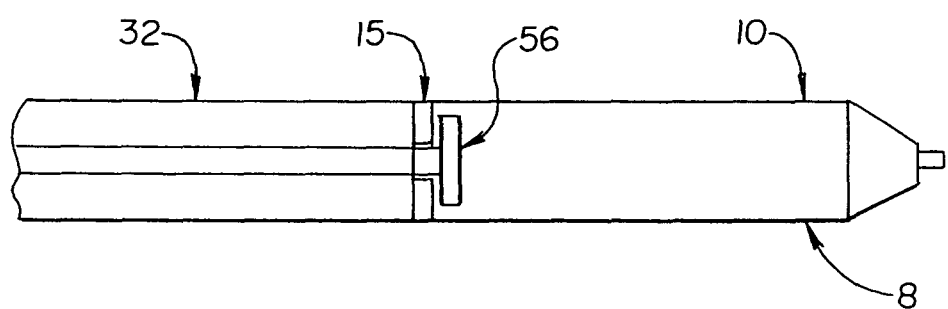
FIG. 21 is a side view of an embodiment of the invention in the engaged state.

It should be noted that most of the clutch mechanisms described in this application may be preassembled such that the proximal member 32 and the distal member 8 are in the engaged state. The distal member 8 may rotate about the clutch extension 48 with pullback means being necessary without the need for a corresponding push means. This is illustrated in FIG. 21 wherein pullback apparatus 56 may not pass through through hole 46 after assembly. It should be recognized that FIG. 21 illustrates only a generic pullback apparatus 56. All of the embodiments in this application may be of the type where substantial movement of the proximal member 32 in relation to clutch housing 15 is inhibited.

Figure 22:
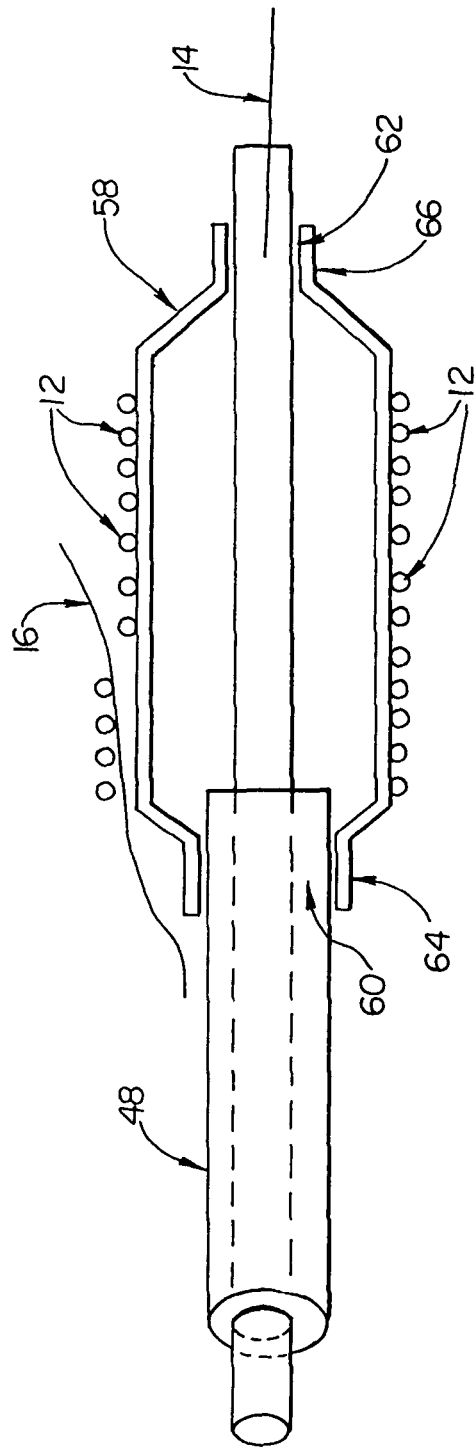
FIG. 22 is a side view of an embodiment of the invention in the unengaged state.

This invention includes the use of balloon expandable stents. Though the use of a sheath has application with balloon expandable stents, in at least one embodiment a sheath is not necessary. As illustrated in FIG. 22 the stent 12 may be disposed about balloon 58 without a sheath. The balloon 58 may be free to rotate about clutch extension 48 in order to better place and deploy the stent. Use at bifurcations is at least one application of this invention. The balloon 58 may be sealingly engaged to the clutch extension 48 at the distal and/or the proximal portions of the balloon 58. In FIG. 22 proximal expandable seal 60 and distal expandable seal 62 are at least partially uninflated.

Figure 23:
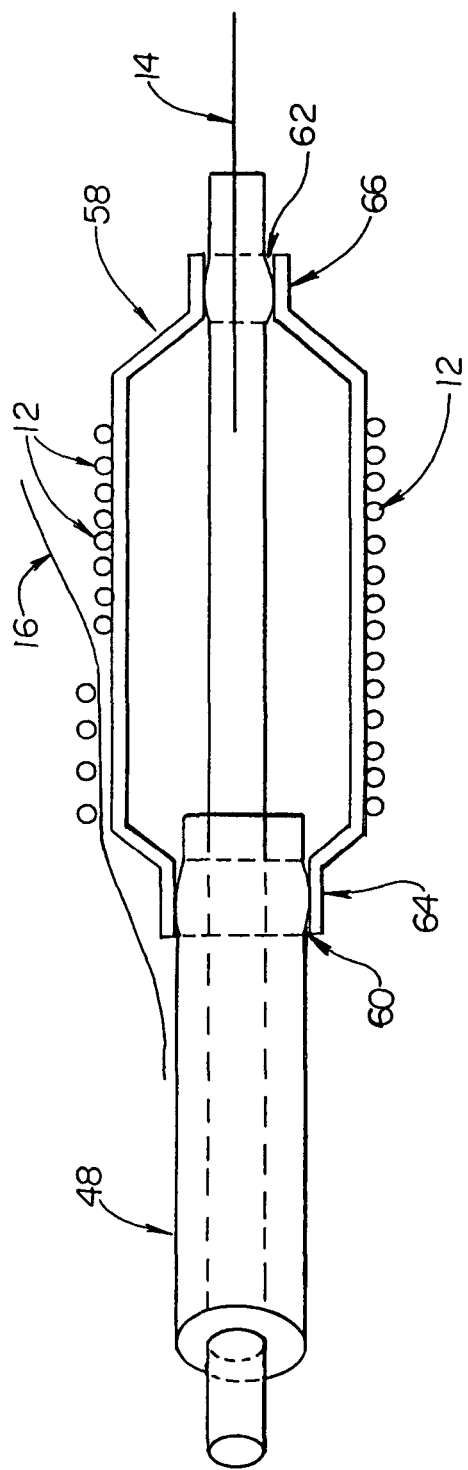
FIG. 23 is a side view of an embodiment of the invention in the engaged state.

Upon positioning the stent 12 the balloon 58 and clutch extension 48 may be moved together proximally by inflating the proximal expandable seal 60 and/or the distal expandable seal 62. The inflated state is shown in FIG. 23. It should be noted that the balloon 58 may rotate in this inflated state.

In some embodiments, as in FIGS. 22 and 23, the clutch extension 48 does not have the proximal member 32 disposed about it at the distal portion of the proximal member 32. In some embodiments the proximal member 32 may be disposed about clutch extension 48 and may extend distally to the proximal end of balloon 58 and in some embodiments be disposed about balloon 58 and stent 12.

In some embodiments, as in FIGS. 22 and 23, the clutch extension 48 has diameters which are unequal at the proximal contacting balloon section 64 and the distal contacting balloon section 66. In some embodiments, clutch extension 48 may be of the substantially same diameter at all locations on the member 48 and longitudinally aligned along all portions of the member 48. In some embodiments, the proximal contacting balloon section 64 and the distal contacting balloon section 66 may have substantially similar diameters. In some embodiments different lumens may be used in inflating the balloon 58, the proximal expandable seal 60, and/or the distal expandable seal 62. In some embodiments the balloon 58, the proximal expandable seal 60, and the distal expandable seal 62 may also share one or more inflation lumens.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A catheter assembly having a longitudinal axis and having an engaged state and an unengaged state when assembled, the catheter assembly comprising:
   a distal member including a stent and a sheath positioned around the stent, the sheath coupled to a clutch housing;
   a clutch extension configured to engage the clutch housing in the engaged state and to disengage the clutch housing in the unengaged state,
   wherein the sheath and the clutch extension are disengaged and substantially moveable independent of one another in the unengaged state, the clutch housing being freely rotatable about the longitudinal axis with respect to the clutch extension when the clutch extension is engaged with the clutch housing in the engaged state, the clutch extension configured to retract the clutch housing and the sheath away from the stent.

2. The catheter assembly of claim 1, wherein the clutch housing is rotatably coupled to a proximal end of the sheath.

3. The catheter assembly of claim 2, wherein the clutch extension is coupled to a wire.

4. The catheter assembly of claim 3, wherein the clutch extension retracts a proximal portion of the sheath from the stent in a proximal direction via the clutch housing.

5. The catheter assembly of claim 1, wherein the clutch extension is configured to disengage from the clutch housing.

6. The catheter assembly of claim 1, wherein the sheath includes a slit.

7. The catheter assembly of claim 6, wherein the slit extends substantially parallel to the longitudinal axis.

8. The catheter assembly of claim 1, wherein the stent is configured as an expandable stent.

9. A catheter assembly having a longitudinal axis and having an engaged state and an unengaged state when assembled, the catheter comprising:
   a distal member positioned along the longitudinal axis, the distal member including a sheath and a clutch housing secured to a proximal end of the sheath, the clutch housing configured to rotate substantially about the longitudinal axis;

a clutch extension positioned proximal of the distal member, the clutch extension configured to move selectively in a proximal direction or in a distal direction relative to the clutch housing to selectively engage and disengage the clutch housing;

wherein the clutch housing is configured to rotate about the longitudinal axis independent of the clutch extension, even when the clutch housing is engaged with the clutch extension when the catheter assembly is arranged in the engaged state;

wherein the clutch extension entrains the sheath to move in the proximal direction or the distal direction when the clutch extension is engaged to the clutch housing when the clutch extension is moved in the proximal direction or the distal direction.

10. A catheter assembly having a longitudinal axis and having an engaged state and an unengaged state when assembled, the catheter assembly comprising:

a proximal member and a distal member, wherein a distal end of the proximal member is removably engageable to the distal member, wherein the distal member has a first distal portion and a second distal portion, the first distal portion constructed and arranged to be retractable from the second distal portion;

wherein, when the catheter assembly is in the unengaged state, the distal member and the proximal member are substantially moveable independent of one another; and wherein, when the catheter assembly is in the engaged state, the distal end of the proximal member is engaged to at least the first distal portion of the distal member and the distal member is substantially freely rotatable about the longitudinal axis in relation to the proximal member, wherein the proximal member is constructed and arranged to be moved in a direction along the longitudinal axis such that proximal movement of the proximal member in the engaged state at least partially retracts the first distal portion of the distal member from the second distal portion.

11. The catheter assembly of claim 10, wherein the distal member comprises a retractable sheath.

12. The catheter assembly of claim 11, wherein the first distal portion comprises the sheath.

13. The catheter assembly of claim 12, wherein the sheath defines a slit, the sheath having edges along the length of the slit.

14. The catheter assembly of claim 13, wherein the slit extends distally from a position on the sheath distal to the proximal most portion of the sheath.

15. The catheter assembly of claim 14, wherein the slit is substantially parallel to the longitudinal axis.

16. The catheter assembly of claim 10, wherein the proximal member is a wire.

17. The catheter assembly of claim 10, wherein the assembly is in the engaged state prior to entry into a lumen.

18. The catheter assembly of claim 17, wherein the proximal member is engaged to the distal member such that the assembly is in the engaged state before entry into the lumen.

19. The catheter assembly of claim 10, wherein the proximal member includes a clutch extension.

20. The catheter assembly of claim 10, wherein the first portion of the distal member includes a clutch housing.

* * * * *